United States Patent [19]
Hise et al.

[11] 3,969,190
[45] July 13, 1976

[54] APPARATUS AND METHOD FOR MICROBIAL FERMENTATION IN A ZERO GRAVITY ENVIRONMENT

[75] Inventors: Ralph E. Hise, Littleton; Russell T. Jordan, Denver, both of Colo.

[73] Assignee: Martin Marietta Corporation, Washington, D.C.

[22] Filed: Aug. 13, 1973

[21] Appl. No.: 387,641

Related U.S. Application Data

[62] Division of Ser. No. 143,808, May 17, 1971, Pat. No. 3,769,176.

[52] U.S. Cl. ............................. 195/142; 195/108; 195/109; 195/139
[51] Int. Cl. ................................................ C12b 1/14
[58] Field of Search ............... 195/1, 15, 105, 108, 195/109, 115, 117, 119, 121, 127, 139, 142

[56] References Cited
UNITED STATES PATENTS

| | | | |
|---|---|---|---|
| 3,186,917 | 6/1965 | Gerhardt et al. | 195/1 |
| 3,418,208 | 12/1968 | Coty | 195/1 |
| 3,586,605 | 6/1971 | Hosler | 195/115 X |
| 3,769,176 | 10/1973 | Hise et al. | 195/142 |

*Primary Examiner*—A. Louis Monacell
*Assistant Examiner*—Robert J. Warden
*Attorney, Agent, or Firm*—Burns, Doane, Swecker & Mathis

[57] ABSTRACT

The growth of micro-organisms, including cells, molds, yeasts, bacteria and the like, under conditions of substantially zero gravity, is accomplished in a closed system maintained within a space vehicle in orbital flight including mechanisms for supplying oxygen of an optimum bubble size range and number density of bubbles, to a suitable culture medium, continuously dialyzing the culture medium of the micro-organism suspension against an excess of fresh culture medium to remove metabolites and replenish nutrients, supplying additional growth medium to the culture as needed, and recovering desired products of the fermentation, including, for example, enzymes, steroids and pharmaceuticals.

12 Claims, 2 Drawing Figures

FIG. I

APPARATUS AND METHOD FOR MICROBIAL FERMENTATION IN A ZERO GRAVITY ENVIRONMENT

This is a division of application Ser. No. 143,808, filed May 17, 1971, now U.S. Pat. No. 3,769,176 issued Oct. 30, 1973.

BACKGROUND OF THE INVENTION

The present invention relates to methods and apparatus for conducting and promoting the propagation and growth, under conditions of substantially zero gravity, of micro-organisms. The term micro-organisms is employed herein as including, for example, cells, molds, yeasts, protozoa, bacteria, and viruses. The term cells is to be understood to include tissues from which the cells are derived, as well as the cells themselves. The invention is concerned primarily with the production or biosynthesis of the metabolic products of the micro-organisms, such products including substances of therapeutic or industrial importance, such as, for example, enzymes, antibiotics, amino acids, vitamins, hormones, and vaccines.

It has been recognized in the prior art that the sustained growth of micro-organisms is limited by the accumulation of toxic metabolites or catabolites, and by the depletion of nutrients in the culture media. In any culture system, in order to prevent the rate of organism proliferation from dropping to zero, fresh growth medium must be supplied at a proper and steady rate so that optimal organism concentration may be maintained by removal of toxic metabolitic products, replenishing necessary nutrients, and removing the products of the fermentation or other growth process, in proportion to their rate of formation. Under earth conditions, these limitations have usually been controlled by the use of various filtration devices, but these have the drawback of low capacity and may readily become clogged.

Data from Biosatellite II experiments have shown that cultures of bacteria grown in a liquid medium under zero gravity conditions in space produce significantly larger populations of bacteria than identical cultures grown on earth. This suggests that fermentation or other analogous growth processes conducted under conditions of zero or near-zero gravity offer a potential for the production of important biologicals or therapeutic substances on a commercial scale with greatly enhanced yield potential in a space vehicle in orbital flight. Under these conditions, advantage is taken of weightlessness to maximize production of the desired products.

The use of a space vehicle for the manufacture of hollow ball bearings and other industrial metal products is proposed in U.S. Pat. No. 3,534,926, and pertinent apparatus is described therein. In U.S. Pat. No. 3,396,084, there is disclosed a test chamber for monitoring the growth and metabolism of cells under zero gravity conditions, but no examples of specific organisms or fermentation processes are mentioned.

GENERAL DESCRIPTION OF THE INVENTION

In accordance with the present invention, there is provided a novel fermentation or other microbiological growth system which is capable of functioning in a remote, zero or near-zero gravity environment, thus taking advantage of weightlessness to maximize production of desired fermentation products. The process of the invention contemplates control of the primary parameters, including temperature, pH, cell concentration, nutrient strength, metabolite concentration, and dissolved oxygen concentration. Critical parameters, particularly where aerobic organisms are involved, are adequacy of oxygen supply, and effective removal of carbon dioxide during fermentation. Under zero gravity conditions it becomes possible to overcome earth-bound limitations of increasing the oxygen concentration level to fully satisfy biological oxygen demand without physical harm to the culture or the resulting end-products, or the presence of concentration gradients in the culture induced by buoyancy or sedimentation, or by extreme turbulency of mixing in conventional fermentation vessels.

Further in accordance with the present invention, there is provided a closed-loop system and apparatus for the culture of micro-organisms under zero or near-zero gravity conditions, including mechanisms for supplying oxygen and removing carbon dioxide, advantageously where the organisms in question are grown in the form of liquid suspension cultures. The culturing is performed in an environment kept continuously in optimal conditions for growth, in which the cell concentration or micro-organism concentration is maintained for any predetermined period of time by the removal of catabolites and the replenishing of nutrients by dialyzing the culture continuously against a large amount of nutrient medium. In this way growth rates can be maintained at high levels for a long, and even an indefinite period of time.

The method of the invention accordingly comprises the steps of (a) providing a suspension of cells, tissue, or other micro-organisms in a suitable culture medium; (b) continuously dialyzing the culture medium of said suspension against an excess of fresh culture medium to remove dialyzable catabolites or metabolites and to replenish dialyzable nutrients; (c) continuously transferring growth medium to the culture at a rate which will insure optimal growth by replenishing nutrients and removing toxic substances; (d) removing cells at a rate which equalizes the growth rate in the culture; and (e) recovering the desired product from the growth stage.

The foregoing fundamental steps in the process of the invention are performed in a substantially zero gravity environment and in equipment which makes special provision for the introduction into the system of oxygen bubbles of minute size which are thus capable of providing oxygen dissolution rates comparable to those produced by intense turbulent mixing under earth gravity conditions. This may be accomplished by employing a sparging device which is capable of forming oxygen bubbles of the desired fine size and numerical density to supply adequate oxygen feed rates to support the growth of the micro-organisms under zero gravity conditions. The sparging device incorporates for this purpose one or more capillary diffusion tubes, or else a perforated or microporous plate having openings of capillary dimensions.

The use of dialysis in microbial fermentations is known in the prior art, and an arrangement of this type is shown, for example, in U.S. Pat. No. 3,186,917, which employs a remote semi-permeable membrane type dialyzer into which there is circulated the micro-organism culture and a diluent to remove toxic fermentation products, on a continuous basis.

In accordance with the process of the present invention there is employed a closed circulation loop fermentation system, in which the culture medium is circulated by two pumps, which may be of any suitable type, such as turbine or peristaltic. The culturing is carried out by providing a body of liquid culture medium in a fermentation zone or chamber of special design, to which nutrient is supplied continuously via dialysis mass transfer. Oxygen in the form of very fine bubbles from a sparger of the type previously described is introduced immediately downsteam from the pump leading from the nutrient supply source. The fermentation and product formation takes place within the main circulation tube or conduit of the system, which thus serves as an elongated fermenter, the entire system being maintained in a zero gravity environment. A portion of the tubular fermenter of suitable length is utilized for the utilization of the growth elements. The culture medium then circulates through a dialyzer to remove metabolites from the medium. During the fermentation most of the supplied oxygen will have been converted to carbon dioxide, which accumulates as bubbles on the fermenter tube surface and is collected and removed via a vent. The basic elements of the closed system zero gravity process concept may be better understood by reference to FIG. 1 of the accompanying drawings, which illustrates a schematic arrangement of apparatus elements constituting the closed loop system.

In accordance with another aspect of the invention, the zero gravity fermentation system may be performed using as a central element a cylindrical fermenter of special design, in which dialysis elements are incorporated in conjunction with agitator elements, and with which vessels for supplying nutrient, substrate, and the like, and for receiving metabolites and for the desired fermentation products are connected as surrounding auxiliaries. A system of this type, which is illustrated in FIG. 2 of the accompanying drawings, is also suitable for operation to perform fermentations and the like under zero gravity conditions.

While the foregoing discussion has been chiefly in terms of the propagation and growth of aerobic micro-organisms, it is to be understood that both the closed fermentation system and the system comprising a central fermentation chamber with auxiliaries are equally adaptable for the propagation and growth of anaerobic micro-organisms such as anaerobic bacteria and others which are capable of carrying out the essential steps involved in the synthesis of nucleotides, nucleic acids, and proteins under zero gravity conditions.

According to the present invention, the propagation and growth of aerobic micro-organisms is favorably affected by the distribution into the liquid culture medium of oxygen gas within a range of bubble size and number density which will result in optimum concentration of the gas and in a minimal tendency for the oxygen to separate from the liquid under conditions of weightlessness or near zero gravity. The bubble size range which appears to be most suitable for the majority of microbial fermentation processes under zero gravity conditions is less than 0.5 mm diameter, e.g., between about 1 micron and 0.2 mm diameter. Similarly the optimum range of number density of the oxygen bubble is greater than 10 bubbles/cm$^3$. As mentioned previously, such bubbles can be suitably obtained by passing a stream of oxygen gas from a suitable supply source through a sparging device having openings of capillary dimensions. The rate at which oxygen is introduced desirably should be sufficient to assure that microbial growth or cell conversion of the substrate is not oxygen limited. An optimum rate for any given micro-organism and set of conversion conditions is best determined empirically for each case by preliminary trial runs. An excess of oxygen normally is not harmful.

GENERAL DESCRIPTION OF THE APPARATUS

Figure 1:
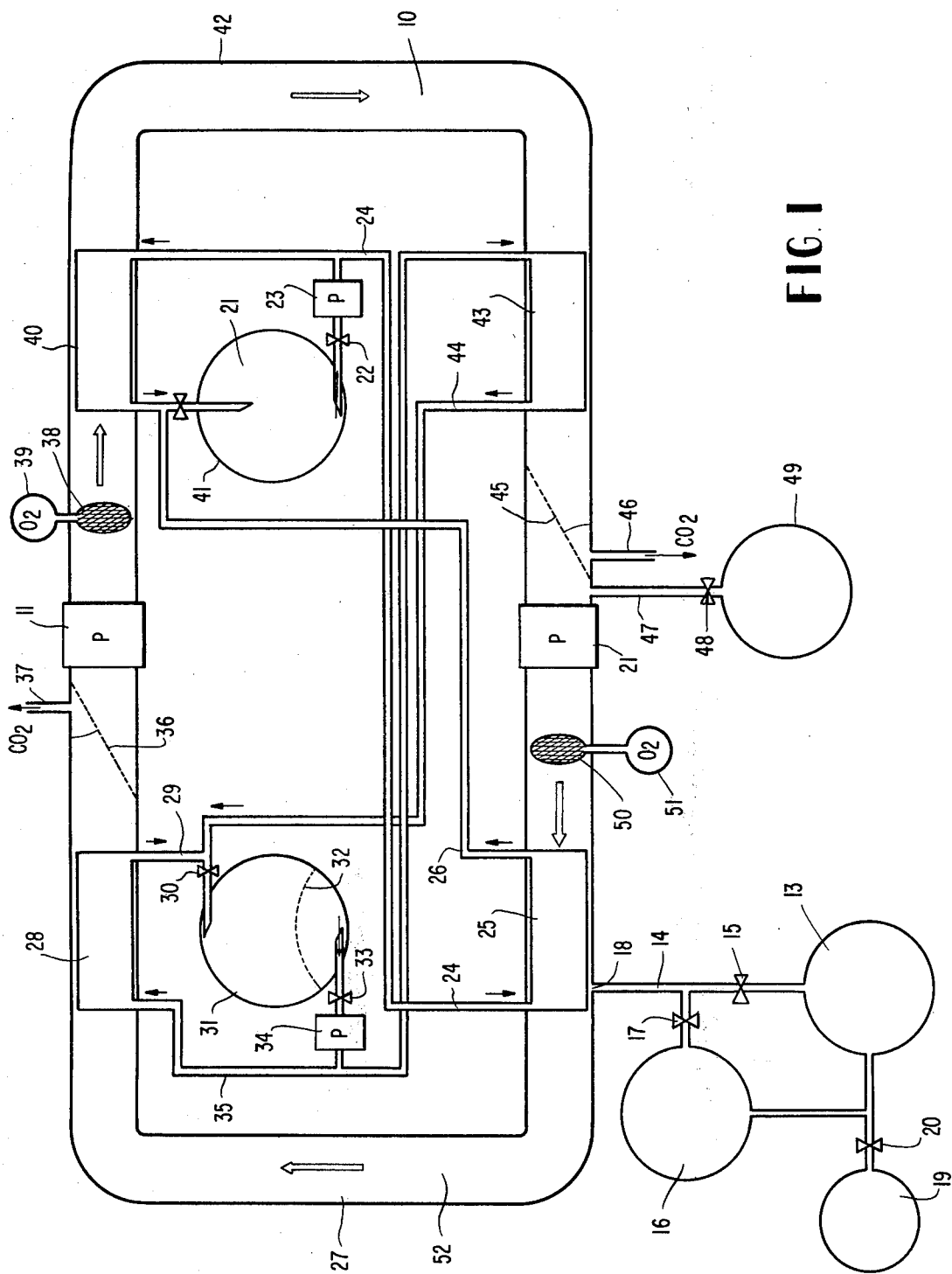
FIG. 1 is a diagrammatic view of fermentation system employing a closed circulation loop.

There is shown in FIG. 1 of the accompanying drawings a closed circulation loop fermentation system, constituting a presently perferred embodiment of this aspect of the invention. In this system the fundamental element is a continuous annular elongated tubular fermenter 10 through which the liquid culture medium is continuously circulated by pumps 11 and 12, which may be of any suitable type such as turbine or peristaltic pumps, both operated from a driving source not shown. Substrate is introduced into the fermenter 10 from a storage vessel 13 via conduit 14 which is controlled by valve 15. Cells or other micro-organisms are introduced into the fermenter from a supply vessel 16 via valve 17 and conduit 14. In either case the initial charge of cell or substrate enters the fermenter at inlet 18. Conveniently, the substrate and/or cell materials are in liquid or suspension form and hence can be injected at inlet 18 by means of a pressure source 19 via control valve 20. Nutrient ingredients necessary to maintain the proper growth conditions in the culture medium are supplied from a reservoir 21 via valve 22 and pump 23, leaving the reservoir via pipe 24, first passing through dialysis membrane mass exchanger 25, which is connected via pipe 26 to return liquid products to nutrient supply reservoir 21.

Fermenter 10 is so constructed as to provide a suitable distance for the utilization of the nutrient growth elements, this portion of the fermenter being designated as 27. When the fermentation has been substantially completed in portion 27 the medium is passed through a filter membrane mass exchanger 28 which serves to remove metabolites, which are passed through conduit 29 via valve 30 into a metabolite accumulator 31, which is provided with a dialysis membrane 32 from which purified filtrate can be returned to the system via valve 33, pump 34, and conduit 35. Upstream from pump 11 is located a screen barrier 36 which serves to trap and separate carbon dioxide and possibly other unconsumed gases which may be present, and these gases are removed from the system via a vent 37. Downstream from pump 11 and in the interior of the fermenter tube, there is positioned a sparger 38 through which a supply of oxygen 39 is continuously introduced into the flowing culture medium. The culture at this point is passed through dialysis membrane mass exchanger 40 which serves to replenish the supply of nutrients in the system by dialysis against a body of nutrient medium 41 contained in reservoir 21. The culture medium with added nutrient passes through portion 42 of the fermenter tube, in which the fermentation is completed, and thence through filter membrane mass exchanger 43 which serves further to remove metabolites which are transmitted therefrom to metabolite accumulator 31 via conduit 44. Thence the culture containing the cells and the desired product of fermentation is passed through a second screen barrier 45 which further serves to remove carbon dioxide bubbles which have accumulated via outlet 46 and the harvest of cells and fermentation products are removed via conduit 47 and valve 48 to cell harvest accumulator 49. The culture medium, which must now be replenished with oxygen and nutrients, passes through pump 12 to a second oxygen sparger 50 located downstream from pump 12 to which oxygen is supplied from a source 51, and a new cycle of the operation commences.

Liquid culture medium 52 circulates through the system and the entire apparatus is located in a zero gravity environment such as that provided in the interior of a space vehicle which may be, for example, in orbital flight at an appropriate distance from the surface of the earth.

Figure 2:
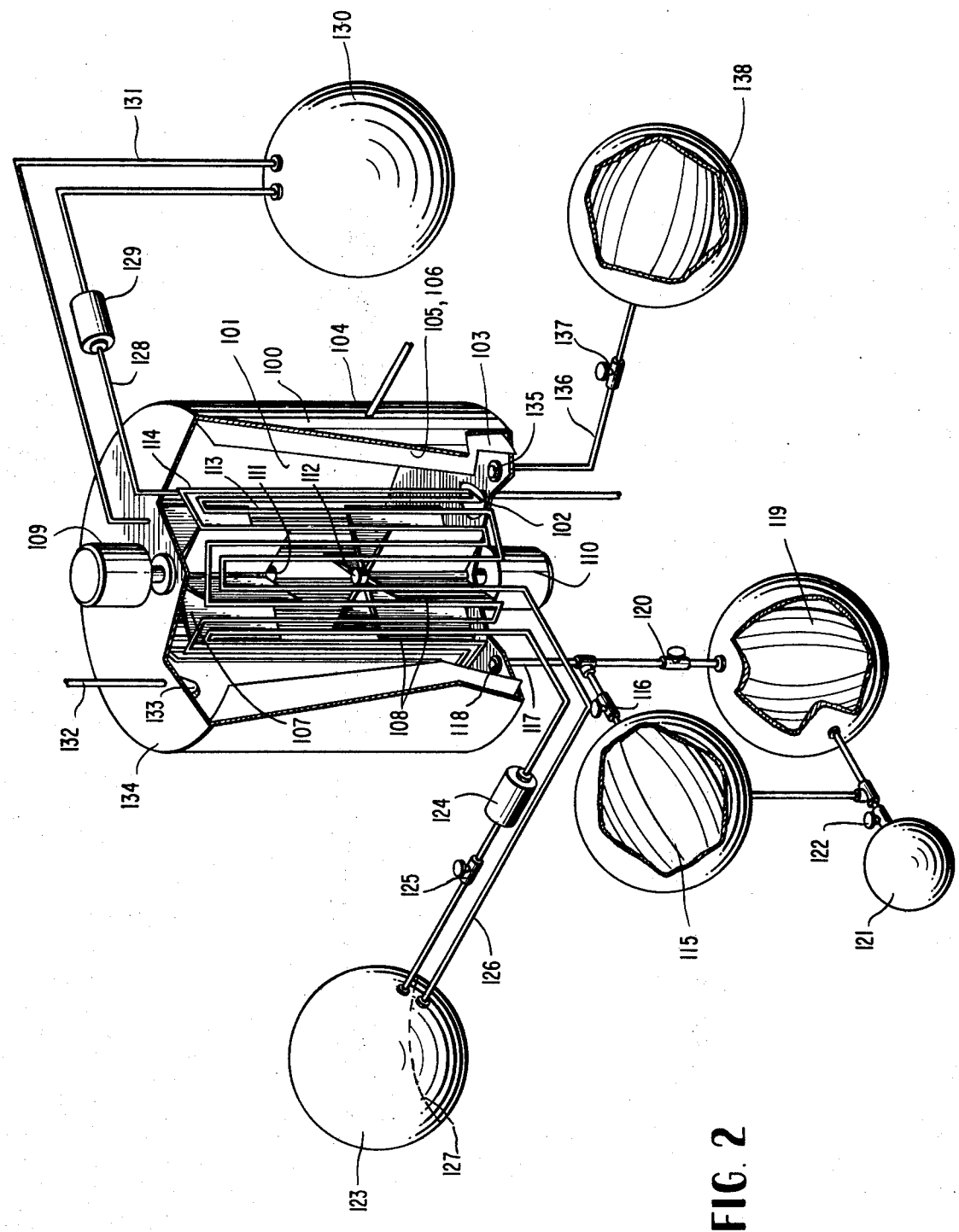
FIG. 2 is a view of a fermentation tank, partially in section, comprising a central cylindrical fermentation portion surrounded by an annular gas jacket, a bubbler for introducing oxygen into the fermentation mass in the central portion and a dialysis membrane for removing carbon dioxide from the central portion.

A second presently preferred embodiment of apparatus for performing microbial fermentations under conditions of zero gravity is the system shown in FIG. 2 of the drawings. This comprises a central fermenter 100 containing a culture 101, which may be generally in the form of a cylindrical tank, provided with a bottom 102, and with a lining portion 103 spaced away from exterior wall 104 of the tank so as to form an annular gas jacket 105 which in turn is provided with vent means shown generally at 106 for removal of accumulated gas. Fermenter 100, in the embodiment shown, is provided with two sets of agitators comprising respectively large paddle blades 107 and 108, which are driven respectively by slow speed motors 109 and 110, connected to central shafts 111 and 112 on which the paddle blades are mounted.

A unique feature is the provision of sets of dialysis tubing 113 and 114, which are mounted on suitable support means (not shown) in such a manner as to be located at the periphery of the sets of paddle blades, but spaced away from them sufficiently to provide clearance. The inner wall 103 of the fermenter comprises a semi-permeable membrane of a silicone elastomer, e.g., a cured, solid, rubbery organosiloxane such as cured RTV 108 made by General Electric Company, or of Teflon (polytetrafluoro ethylene), through which accumulated $CO_2$ and other gases may diffuse into the gas jacket. The location of the dialysis tubing results in optimum nutrient and metabolite mass transfer.

The central fermenter 100 is provided with the following auxiliary supply and removal means:

Fresh micro-organisms are introduced into the fermenter from storage vessel 115 via valve 116 and conduit 117, entering the bottom of the tank at inlet 118. Substrate is supplied from storage vessel 119 via valve 120 and conduit 117 and inlet 118. Both micro-organism and substrate supply are maintained from a pressure source 121 connected via valve 122 to vessels 115 and 119, respectively.

Of the dialysis tubes, set 113 is connected to metabolite reservoir 123 via pump 124 and valve 125 and return conduit 126; the metabolite reservoir or accumulator is provided in the interior thereof with a fine dialysis membrane 127 which keeps the circulating fluid therein clean for the culture medium. The second set of dialysis tubes 114 is connected via conduit 128 and pump 129 to nutrient supply reservoir 130 and return conduit 131. Oxygen gas is supplied under pressure as required via conduit 132 and sparger 133 located in the interior of the tank just below the top portion 134 thereof. Cell harvester and fermentation products are removed from the tank via outlet 135, conduit 136 and valve 137 to accumulator vessel 138 from which the products may be suitably removed.

The entire system is maintained in a zero or near zero gravity environment which may be, for example, the interior of a space vehicle in orbital flight at a suitable distance from the surface of the earth, or it may be the surface of a small planet such as the Moon.

DESCRIPTION OF THE PREFERRED EMBODIMENTS

In addition to the presently preferred apparatus embodiments described above, the following examples illustrate the practice of the processes of the invention but are not to be regarded as limiting:

EXAMPLE 1

Production of Bacteria

Utilizing the apparatus of FIG. 2 and maintaining substantially zero gravity conditions, the organism *Pseudomonas graveolens* is grown for the production, by bacterial action, of maltobionic acid and lactobionic acid, the calcium salts of which are useful in calcium therapy. The culture medium containing 278 grams of anhydrous lactose is inoculated with 100 ml. culture of *Pseudomonas graveolens* 14 containing 10 grams of anhydrous lactose. After inoculation such a nutrient solution will contain:

Anh. lactose — 288 grams
$KH_2PO_4$ — 1.86 grams
$MgSO_4.7H_2O$ — 0.775 grams
Urea — 6.2 grams
Corn steep liquor — 15 ml.
Soya oil (antifoam agent) — 1 ml.
$CaCO_3$ — 83 grams This solution is placed in the fermenter and maintained during the bacterial action at 25°C. and a stream of oxygen bubbles having a nominal diameter of 0.1 mm is passed in at the rate of approximately 96 ml. per minute. The resultant solution will contain lactobionic acid as the calcium salt in a yield which is substantially greater than the yield of 77% that is representative of results obtained under earth gravity conditions.

EXAMPLE 2

Production of Enzymes

This example illustrates the production of bacterial enzymes by the cultivation of micro-organisms such as *Bacillus subtilis*, also utilizing the apparatus of FIG. 2. The nutrient medium is one which contains more than 40 parts of carbohydrate-containing substances to 1 part of assimilable nitrogen. The culture medium contains 3% starch, 0.02% nitrogen in the form of ammonium sulfate, and 8 parts per thousand of a mixture of $KH_2PO_4$ and $K_2HPO_4$ as a buffer, the solution having a pH of 7.1. It is inoculated with a culture of an amylase-forming bacterial organism of the group Mesentericus and aerated with oxygen bubbles having an approximate nominal diameter of 0.05 mm at 28°C. at a rate sufficient to assure that the cell conversion of the substrate is not oxygen limited. The enzyme is collected in the cell harvest accumulator.

EXAMPLE 3

Production of Steroid Hormones

Utilizing the apparatus of FIG. 1 and the process for the production of 11-oxygenated steroids disclosed in U.S. Pat. No. 2,602,769, there is employed the oxidizing fungal enzyme produced by the action of a fungus of the order Mucorales, specifically the organism R-4 *Rhizopus nigricans* ATCC 6227 b. The fermentation is performed utilizing finely divided oxygen having a nominal bubble diameter of 0.1 mm, the oxygen being introduced at a rate slightly in excess of the rate at which it is consumed in the fermentation reaction. Examples of 11-oxygenated steroids which can be thus produced include corticosterone, 11-dehydro corticosterone, and cortisone.

What is claimed is:

1. Apparatus for conducting the propagation and growth of micro-organisms in a substantially zero gravity environment and for the recovery of fermentation products therefrom comprising:
    closed circulation loop fermenter means for containing a liquid culture suspension;
    circulating means operably connected to said fermenter means for circulating said liquid culture suspension within said fermenter means;
    means for supplying nutrients, said means including a nutrient reservoir and first dialysis means;
    means for accumulating metabolic products from said fermenter means, said means including a metabolic product reservoir and second dialysis means;
    means for introducing oxygen into said fermenter means;
    means for removing carbon dioxide gas from said fermenter means; and,
    means for collecting micro-organism cells and fermentation products from said fermenter means.

2. Apparatus as defined in claim 1 including means for supplying growth substrate to said fermenter means.

3. Apparatus as defined in claim 1 wherein said means for introducing oxygen into said fermenter means includes at least one capillary oxygen sparger positioned within the interior of said fermenter means for supplying oxygen to said fermenter means in the form of fine bubbles.

4. Apparatus as defined in claim 1 wherein said oxygen introducing means includes at least one pair of capillary oxygen spargers at approximately diametrically opposed locations.

5. Apparatus as defined in claim 1 wherein said means for removing carbon dioxide gases includes at least one pair of screen barriers to the liquid culture at approximately diametrically spaced locations.

6. Apparatus as defined in claim 1 wherein said circulation means includes at least one pair of pumps positioned at approximately diametrically remote locations for continuously circulating the liquid culture medium within said fermenter.

7. Apparatus as defined in claim 1 wherein said first and second dialysis means includes dialysis membrane mass exchangers positioned within said closed circulation loop fermenter at approximately diametrically opposed locations.

8. Apparatus as defined in claim 7 wherein said oxygen introducing means includes at least one pair of capillary oxygen spargers at approximately diametrically opposed locations.

9. Apparatus as defined in claim 8 wherein said means for removing carbon dioxide gases includes at least one pair of screen barriers to the liquid culture at approximately diametrically spaced locations.

10. Apparatus for conducting the propagation and growth of micro-organisms in a substantially zero gravity environment and for the recovery of fermentation products therefrom comprising:
    closed circulation loop fermenter means for containing a liquid culture suspension;
    means operably connected to said fermenter means for providing circulation of said liquid culture suspension within said means;
    a nutrient supply reservoir;
    first dialysis means positioned within the interior of said fermenter means;
    means connecting said first dialysis means to said nutrient supply reservoir;
    means connected to said means connecting said first dialysis means to said nutrient supply reservoir for circulating a nutrient between said nutrient supply reservoir and said first dialysis means;
    a reservoir for accumulating metabolic products;
    second dialysis means positioned within the interior of said fermenter means;
    means connecting said second dialysis means to said reservoir for accumulating metabolic products;
    means connected to said means connecting said second dialysis means to said reservoir for accumulating metabolic products for circulating a fluid between said reservoir for accumulating metabolic products and said second dialysis means;
    means connected to said fermenter means for introducing oxygen into the interior of said fermenter means:
    means connected to said fermenter means for removing from within the interior of said fermenter means carbon dioxide gas produced during a fermentation process; and
    a vessel connected to said fermenter for removing and collecting micro-organism cells and fermentation products from said fermenter means.

11. Apparatus as defined in claim 10 wherein said first and second dialysis means includes dialysis membrane mass exchangers positioned within said closed circulation loop fermenter at approximately diametrically opposed locations.

12. The apparatus of claim 10 wherein said carbon dioxide gas removing means includes at least one pair of screen barriers to the liquid culture at approximately diametrically spaced locations.

* * * * *